(12) United States Patent
Gross et al.

(10) Patent No.: US 10,004,887 B2
(45) Date of Patent: Jun. 26, 2018

(54) TRANSDERMAL DELIVERY ASSEMBLY

(71) Applicant: Alma Therapeutics Ltd., Petach-Tikva (IL)

(72) Inventors: Yossi Gross, Moshav Mazor (IL); Oz Cabiri, Hod-HaSharon (IL)

(73) Assignee: ALMA THERAPEUTICS LTD., Petach-Tikva (IL)

( * ) Notice: Subject to any disclaimer, the term of this patent is extended or adjusted under 35 U.S.C. 154(b) by 34 days.

(21) Appl. No.: 14/624,721

(22) Filed: Feb. 18, 2015

(65) Prior Publication Data

US 2016/0235957 A1   Aug. 18, 2016

(51) Int. Cl.
*A61B 17/20* (2006.01)
*A61M 37/00* (2006.01)

(52) U.S. Cl.
CPC . *A61M 37/0015* (2013.01); *A61M 2037/0007* (2013.01); *A61M 2037/0023* (2013.01); *A61M 2037/0061* (2013.01)

(58) Field of Classification Search
CPC ...... A61M 37/0015; A61M 2037/0023; A61M 2005/1585; A61M 2210/04
USPC ........................................... 604/22–27, 890.1
See application file for complete search history.

(56) References Cited

U.S. PATENT DOCUMENTS

| | | | | |
|---|---|---|---|---|
| 5,190,558 A | * | 3/1993 | Ito | A61B 17/322 |
| | | | | 604/289 |
| 6,589,202 B1 | * | 7/2003 | Powell | A61B 10/0045 |
| | | | | 604/27 |
| 2004/0087992 A1 | * | 5/2004 | Gartstein | A61B 17/205 |
| | | | | 606/186 |
| 2008/0220092 A1 | | 9/2008 | Dipierro et al. | |
| 2012/0302942 A1 | | 11/2012 | DiPierro et al. | |
| 2013/0144261 A1 | | 6/2013 | Chowdhury | |
| 2014/0200525 A1 | | 7/2014 | DiPierro | |
| 2014/0207047 A1 | | 7/2014 | DiPierro et al. | |
| 2014/0207048 A1 | | 7/2014 | DiPierro et al. | |
| 2014/0323423 A1 | | 10/2014 | DiPierro et al. | |

FOREIGN PATENT DOCUMENTS

| | | | |
|---|---|---|---|
| GB | 2448493 A  * | 10/2008 | ........ A61M 37/0015 |
| WO | WO 2016/132368 | 8/2016 | |

OTHER PUBLICATIONS

International Search Report and the Written Opinion dated Jun. 5, 2016 From the International Searching Authority Re. Application No. PCT/IL2016/050196.

Harapanhalli "Scientific and Regulatory Challenges of Transdermal Drug Delivery Systems (TDDS) and Relevance of Quality-by-Design (QbD) Approach to Their Development", Presented to the Advisory Committee for Pharmaceutical Science and Clinical Pharmacology, FDA, U.S, Food Drug Administration, Silver Spring, MD, USA, Aug. 5, 2009, p. 1-38, Aug. 2009.

(Continued)

*Primary Examiner* — Phillip Gray
(74) *Attorney, Agent, or Firm* — The Roy Gross Law Firm, LLC; Roy Gross

(57) ABSTRACT

An assembly includes a patch including a substance adapted for transdermal delivery, and a driver operative to move the patch to one or more of a plurality of operational relationships with a skin of a patient, including being in full contact with the skin, partial contact with the skin, and no contact with the skin.

34 Claims, 8 Drawing Sheets

(56) References Cited

OTHER PUBLICATIONS

Sadrieh "Challenges in the Development of Transdermal Drug Delivery Systems", Presented to the Advisory Committee for Pharmaceutical Scinece and Clinical Pharmacology, FDA, U.S. Food and Drug Administration, Silver Spring, MD, USA, Aug. 5, 2009, p. 1-17, Aug. 2009.

* cited by examiner

TRANSDERMAL DELIVERY ASSEMBLY

FIELD OF THE INVENTION

The present invention relates generally to a method and apparatus for transdermal delivery of a substance.

BACKGROUND OF THE INVENTION

The skin is made up of several layers with the upper composite layer being the epithelial layer. The outermost layer of the skin is the stratum corneum which has well known barrier properties to prevent molecules and various substances from entering the body and analytes from exiting the body. The stratum corneum is a complex structure of compacted keratinized cell remnants having a thickness of about 10-30 microns. The stratum corneum forms a waterproof membrane to protect the body from invasion by various substances and the outward migration of various compounds.

The natural impermeability of the stratum corneum prevents the administration of most pharmaceutical agents and other substances through the skin. Numerous methods and devices have been proposed to enhance the permeability of the skin and to increase the diffusion of various drugs through the skin so that the drugs can be utilized by the body. Typically, the delivery of drugs through the skin is enhanced by either increasing the permeability of the skin or increasing the force or energy used to direct the drug through the skin. Examples include the use of micro-needles, laser ablation, RF ablation, heat ablation, sonophoresis, iontophoresis, or a combination thereof.

In some cases, these treatments are provided by a single integrated device that performs two separate functions: the device treats the skin and also delivers an active ingredient to the treated skin. An example is a hollow micro-needle array with an attached drug reservoir.

Transdermal patches are well known and in wide use for many purposes, such as but not limited to, hormonal therapy, narcotic analgesia, nicotine and many others. However, transdermal patches have drawbacks and patch administration can be complicated. For example, many patients fail to remove the overlay or protective liner in order to expose the adhesive and medication to the skin for absorption. Of course, the result is the medicine is not administered to the patient. Another problem is overdose; applying too many patches at one time can be fatal (e.g., fentanyl overdose). Another problem is changing the patch for a fresh patch at the wrong time interval, thereby causing improper dosage of the medicine. Accordingly, patient compliance in using transdermal patches is a critical problem facing caregivers (especially for elderly patients) and pharmaceutical firms alike.

In summary, it is often difficult to achieve proper time duration of patch application, proper intervals between dosages and proper dosing strengths.

SUMMARY OF THE INVENTION

The present invention seeks to provide a novel transdermal delivery assembly, as is described more in detail hereinbelow. The transdermal delivery assembly solves the problems of the prior art by providing control of the time duration during which the patch administers the substance, control of the time intervals between dosages and control of the dosing strengths. The system is user-friendly and much less prone to user mistakes than the prior art.

In one embodiment, the transdermal delivery assembly includes a patch including a substance adapted for transdermal delivery. For example, the assembly can use any commercially available transdermal patch impregnated or otherwise provided with a substance. Accordingly, the system can use the same approved transdermal patch from an approved patch supplier with the previously unknown feature of controlled time delivery and cessation of delivery.

The patch is mounted on a substrate which is driven by a driver. The driver moves the patch to one or more of a plurality of operational relationships with the skin of the patient, including being in full contact with the skin (i.e., the entire area of patch is in contact with the skin), being in partial contact with the skin (i.e., only a portion of the total area of patch is in contact with the skin), and not being in contact with the skin.

In one embodiment, the operation of the driver is controlled by a controller that controls when and for how long the patch is in a particular operational relationship with the skin (e.g., at what time of the day is the patch in full, partial or no contact with the skin and for what duration of time).

The system of the invention can apply or peel the patch from the skin at certain times for certain time durations, even while the user is asleep or incapacitated. The amount of substance administered can be optimized independently of the time of the patch application. The system can be operated based on a real time clock. The system can be operated with a wireless/cellular connection, which may be helpful for use with children or the elderly. For example, the system may load the patch to a safe position (no substance administration) and then later released (that is, moved to an operational position where the substance is delivered) by authorized personnel (e.g., parent or caregiver).

The system of the invention may be particularly advantageous in "chronotherapy", in which drug delivery is timed in accordance with circadian rhythms of the body or circadian rhythms of a disease, in order to optimize therapeutic efficacy and minimize side effects. The dose control may be programmed to accurately and automatically deliver redefined doses that coincide with peak disease symptoms. This can be important when symptoms peak at night while asleep or immediately upon waking.

Circadian rhythms are physical, mental and behavioral changes that follow a roughly 24-hour cycle, responding primarily to light and darkness in an organism's environment. Circadian rhythms can influence sleep-wake cycles, hormone release, body temperature and other important bodily functions. They have been linked to various sleep disorders, such as insomnia. Abnormal circadian rhythms have also been associated with obesity, diabetes, depression, bipolar disorder, seasonal affective disorders, asthma attacks, coronary infarction, angina pectoris, stroke and ventricular tachycardia, among others. The system can be used to transdermally deliver active drugs (propranolol, nifedipine, verapamil, enalapril, isosorbide 5-mononitrate and digoxin), anti-asthmatics (theophylline and terbutaline), anticancer drugs, psychotropics, analgesics, local anesthetics and antibiotics.

There is thus provided in accordance with a non-limiting embodiment of the present invention an assembly including a patch having a substance adapted for transdermal delivery; and a driver operative to move the patch to one or more of a plurality of operational relationships with a skin of a patient, the operational relationships including being in full contact with the skin, partial contact with the skin, and no contact with the skin. A controller may control the driver so as to control when and for how long the patch is in one or more of the operational relationships with the skin.

The patch may be mounted on a substrate driven by the driver. The substrate may be mounted on one or more rollers.

In accordance with a non-limiting embodiment of the present invention the substrate further includes a non-patch zone. The non-patch zone may include a stratum corneum resurfacing element. The driver may be operative to drive more than one patch.

The patch and the stratum corneum resurfacing element may be arranged to move synchronously with each other.

The driver may be operatively linked to move the patch via a friction drive, gear drive or male-female connection or other suitable device. The patch (and the stratum corneum resurfacing element) may be located peripherally outwards of the driver.

The stratum corneum resurfacing element may include an adhesive surface operative to attach to and peel a portion of stratum corneum. Alternatively or additionally, the stratum corneum resurfacing element may include a chemical (e.g., glycolic acid or salicylic acid) operative to peel a portion of stratum corneum. Alternatively or additionally to any combination of the above, the stratum corneum resurfacing element may include a micro-needle array. The patch may be slotted so that the patch can move in an angular motion.

BRIEF DESCRIPTION OF THE DRAWINGS

The present invention will be understood and appreciated more fully from the following drawings.

DETAILED DESCRIPTION OF EMBODIMENTS

Reference is now made to FIGS. 1A-1E, which illustrate a transdermal delivery assembly 10, constructed and operative in accordance with a non-limiting embodiment of the present invention.

The transdermal delivery assembly 10 includes a patch 12 including a substance adapted for transdermal delivery. Patch 12 may be any commercially available transdermal patch impregnated or otherwise provided with a substance (e.g., drug). The transdermal delivery assembly 10 may be provided by the manufacturer as a hermetically sealed assembly, which obviates the need for liners and backings to protect the patch. Alternatively, patch 12 may have a backing that protects the patch from the outer environment, as well as a liner which is removed prior to installing the patch in the device. One way of removing such a liner is described further below with reference to FIGS. 6A-6C. As is known in the art, patch 12 may include a permeation enhancer for enhancing delivery of the substance through the stratum corneum.

Figure 1A:
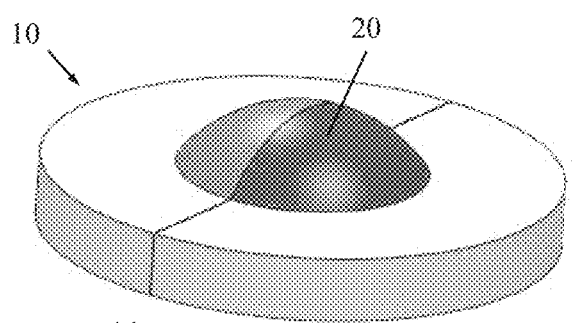
FIG. 1A is a simplified pictorial illustration of a transdermal delivery assembly, constructed and operative in accordance with a non-limiting embodiment of the present invention.
Figure 1B:
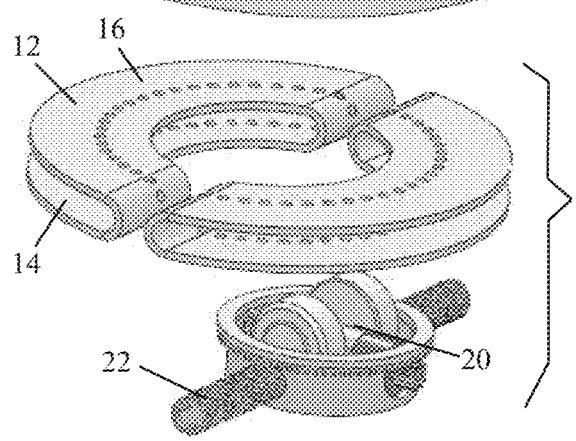
FIG. 1B is a simplified pictorial illustration of inner components of the transdermal delivery assembly including a patch, stratum corneum resurfacing element and driver.
Figure 1C:
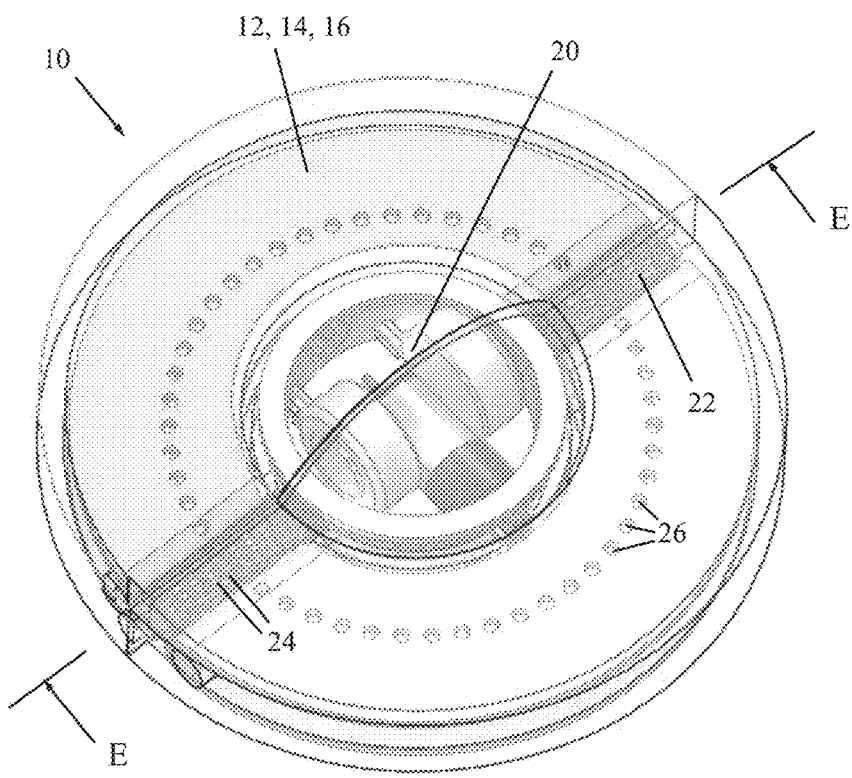
FIG. 1C is a simplified top, transparent view of the transdermal delivery assembly.
Figure 1D:
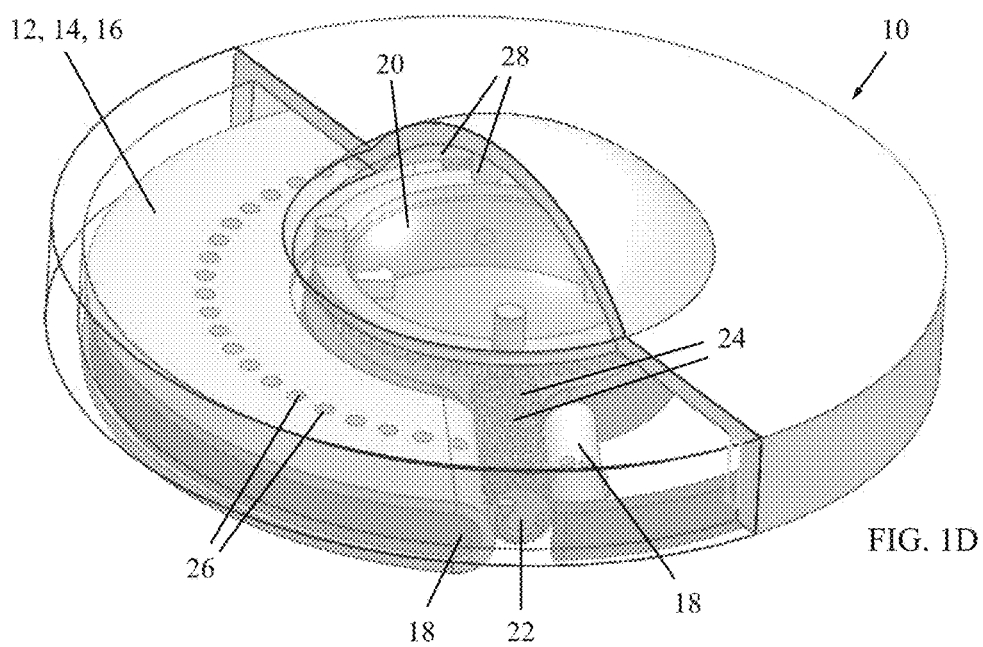
FIG. 1D is a simplified perspective cutaway view of the transdermal delivery assembly.
Figure 1E:
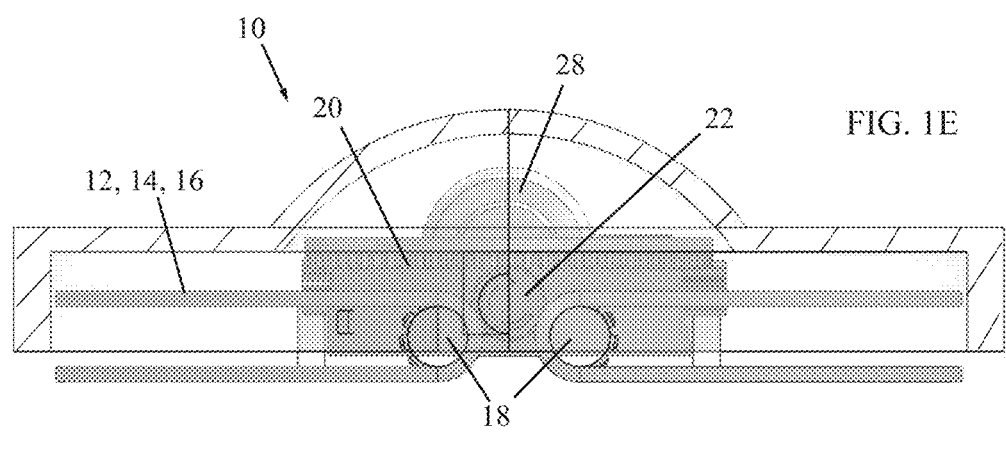
FIG. 1E is a simplified sectional view of the transdermal delivery assembly, taken along lines E-E in FIG. 1C.

Patch 12 is mounted on a substrate 16 which is driven by a driver 20. As will be described more in detail, driver 20 moves patch 12 to one or more of a plurality of operational relationships with the skin of the patient, including being in full contact with the skin (i.e., the entire area of patch 12 is in contact with the skin), being in partial contact with the skin (i.e., only a portion of the total area of patch 12 is in contact with the skin), and not being in contact with the skin. In one embodiment, the operation of driver 20 is controlled by a controller 28 (FIG. 1D). Controller 28 governs the speed of driver 20 and thereby controls when and for how long patch 12 is in a particular operational relationship with the skin (e.g., at what time of the day is patch 12 in full, partial or no contact with the skin and for what duration of time). In some embodiments, driver 20 and controller 28 can vary the amount of pressure applied to patch 12 against the skin; e.g., the more patch 12 is pressed against the skin, the greater the rate of substance delivery per unit time. The driver 20 and controller 28 stabilize or control the transfer rate of the substance from the patch 12 by causing the patch to contact fresh areas on the skin and thereby compensate for degradation of the substance concentration in older or previous areas on the skin.

In the illustrated embodiment, substrate 16 is a continuous belt rotatably mounted on a roller 18. As seen best in FIG. 1D, driver 20 may be a motor with an output shaft 22 that meshes with the movable element (e.g., roller) 18 or directly with substrate 16. For example, movable element 18 may be a gear and output shaft 22 may be complimentary shaped (e.g., having worm threads) to mesh with and turn movable element 18. Alternatively, output shaft 22 may be linked to movable element 18 via a friction drive.

Alternatively, as shown in the illustrated embodiment, output shaft 22 may be linked to movable element 18 via a male-female connection. Output shaft 22 may be provided with pins or teeth 24 (male part) that engage holes 26 (female part) formed in substrate 16. Teeth 24 and holes 26 are also referred to as drive interface elements. In all of the above examples, as driver 20 turns output shaft 22, the substrate 16 is caused to turn about rollers 18.

In one embodiment, substrate 16 only includes the patch 12, which wraps around roller or rollers 18. In such an embodiment, as the patch rolls on the skin, the patch sometimes fully contacts the skin and sometimes partially contacts the skin.

In another embodiment, substrate 16 not only includes patch 12, but also a non-patch zone 14. Non-patch zone 14 may be simply a blank area on substrate 16.

In another embodiment, the non-patch zone 14 is a stratum corneum resurfacing element 14 (for "skin activation" or "skin resurfacing"). The stratum corneum resurfacing element 14 may include an adhesive surface operative to attach to and peel a portion of stratum corneum. Alternatively or additionally, the stratum corneum resurfacing element may include a chemical (e.g., glycolic acid or salicylic acid) operative to peel a portion of stratum corneum. Alternatively or additionally to any combination of the above, the stratum corneum resurfacing element may include a microneedle array. In such an embodiment, as the patch rolls on the skin, the patch sometimes fully contacts the skin (at which time the non-patch zone 14 may not contact the skin at all, but alternatively can be configured to partially or fully contact the skin, too), sometimes partially contacts the skin (at which time the non-patch zone 14 may partially contact the skin, but alternatively can be configured for no contact or full contact) and sometimes does not contact the skin at all (at which time the non-patch zone 14 may fully contact the skin (but alternatively can be configured for no contact or partial contact).

In this arrangement, patch 12 and stratum corneum resurfacing element 14 move synchronously with each other. In the illustrated embodiment, there are two substrates 16 (mirror images of each other) arranged to roll on two rollers 18; the substrates form two halves of a round, compact assembly 10. The patches 12 and stratum corneum resurfacing elements 14 are located peripherally outwards of driver 20. Thus, one driver 20 is operative to drive more than one patch 12 and more than one stratum corneum resurfacing element 14.

The controller 28 (FIG. 1D) may be provided internally in (or externally to) assembly 10 for controlling operation of driver 20. The control electronics 28 may be pre-programmed to activate driver 20 continuously, incrementally or a combination thereof in accordance with a treatment plan. A battery (not shown) may be used to energize driver 20.

The patch can be also driven manually by rotating the cover of the assembly which may be connected to the drive mechanism (e.g., gear, friction, male-female drive).

In one embodiment, the roller 18 has a perimeter larger than the size (rolling length) of the patch 12. In this manner, the moving and rolling speeds of the device are synchronized.

Other methods may be implemented in the invention for moving the patch with a driver to change the amount of patch area touching the skin. For example, in another embodiment, the patch is mounted on a substrate but not on a roller, and the driver is operative to grasp and move the substrate. The substrate is arranged to be lifted off the skin by the driver, such as being moved perpendicularly off the skin or by gradually peeling the patch at an angle and lifting the patch off the skin, and then afterwards re-attaching the patch to the skin, either at the same place or a different place. The driver may, for example, include pincers or slender jaws and the like for grasping the substrate and patch. The driver can move the patch linearly and/or rotationally.

Figure 2:
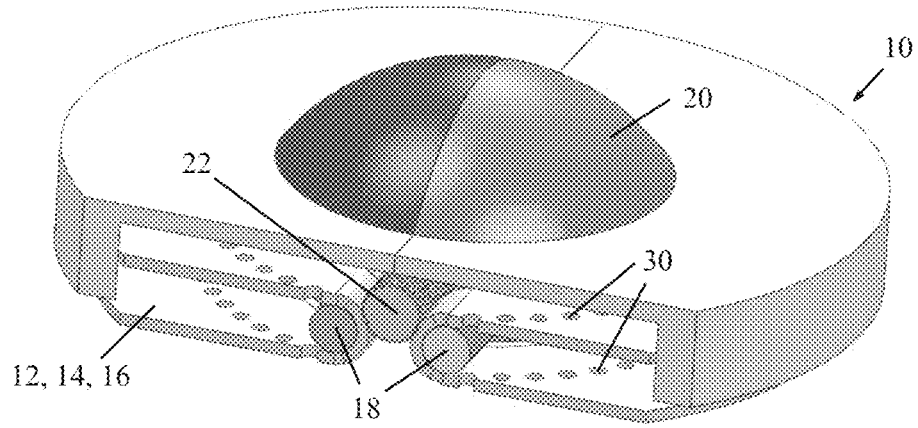
FIG. 2 is a simplified pictorial illustration of the transdermal delivery assembly, showing an additional set of drive interface elements for enhancing torque to move the patch and stratum corneum resurfacing element.

Reference is now made to FIG. 2, which illustrates an additional set of drive interface elements for enhancing torque to move patch 12 and stratum corneum resurfacing element 14. For example, the additional set of drive interface elements may include another set of holes 30 that receive torque from driver 20 and move substrate 16 as in a tracked-wheel mechanism.

Figure 3A:
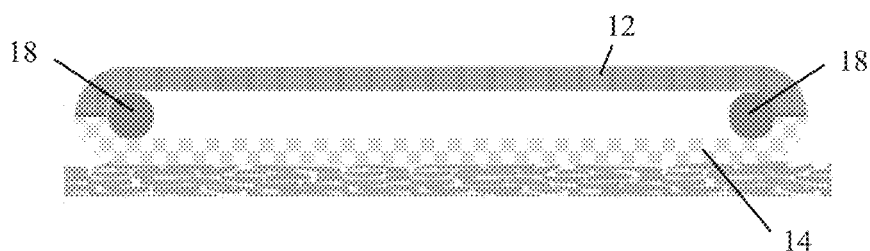
FIGS. 3A, 3B and 3C are simplified pictorial illustrations of progressive movement of the patch and stratum corneum resurfacing element, in accordance with an embodiment of the present invention.
Figure 3B:
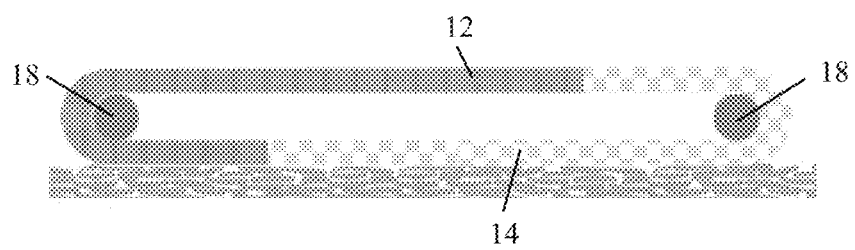
Figure 3C:
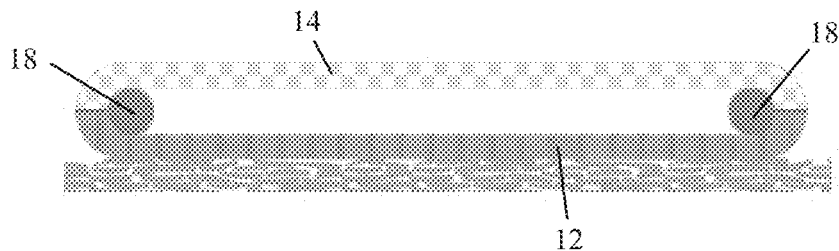

Reference is now made to FIGS. 3A, 3B and 3C, which illustrate progressive movement of patch 12 and stratum corneum resurfacing element 14. In FIG. 3A, patch 12 with the substance is above rollers 18 and stratum corneum resurfacing element 14 is below rollers 18. In FIG. 3B, the substrate 16 has turned so that patch 12 is partially turned below rollers 18 and stratum corneum resurfacing element 14 is partially above rollers 18. In FIG. 3C, the substrate 16 has turned so that patch 12 is now below rollers 18 and stratum corneum resurfacing element 14 is now above rollers 18. As stratum corneum resurfacing element 14 contacts the stratum corneum and continues to turn off the skin, it peels off a portion of the stratum corneum, so that when patch 12 turns to contact the skin the patch contacts a resurfaced skin. In this manner, the stratum corneum has been resurfaced and been made more susceptible to transdermal delivery of the substance through the skin.

Figure 4:
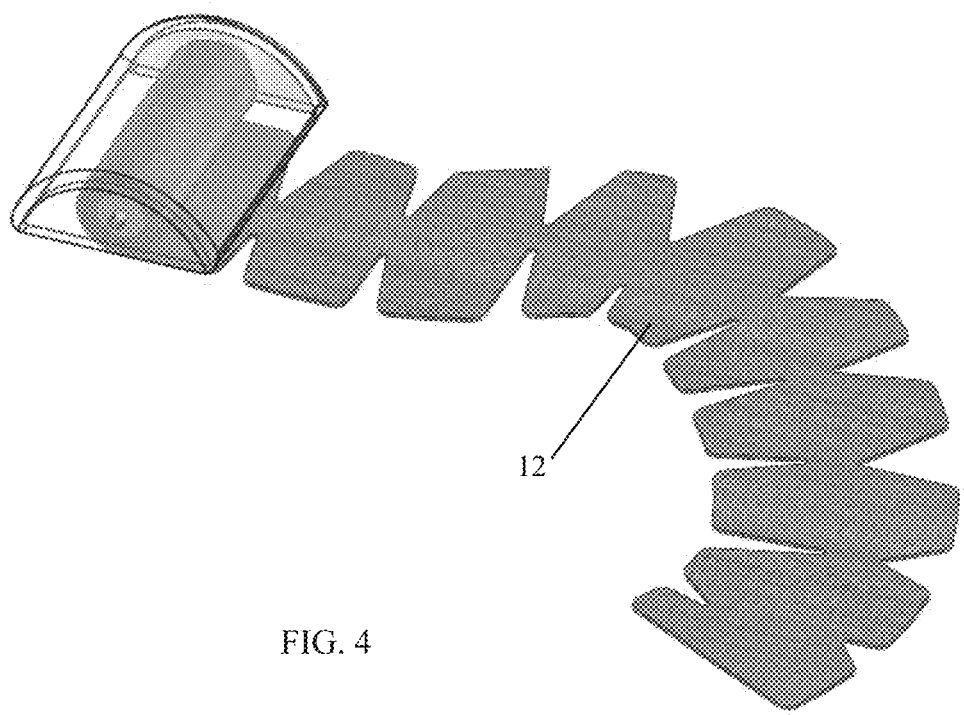
FIG. 4 is a simplified pictorial illustration of the patch being slotted so that the patch can move in an angular motion in accordance with an embodiment of the present invention.

FIG. 4 shows that patch 12 may be slotted or otherwise shaped so that patch 12 can move in an angular motion.

Figure 5A:
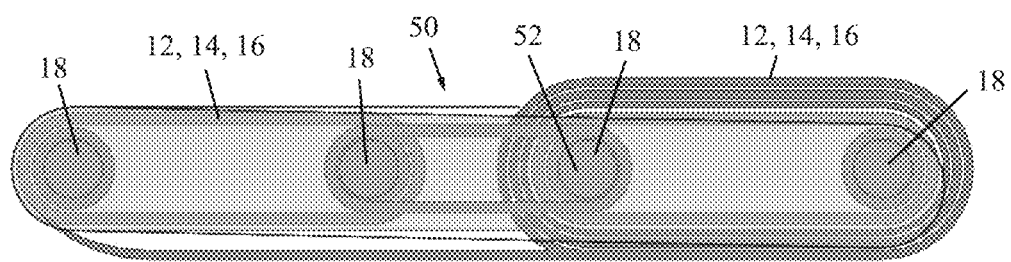
FIGS. 5A and 5B are simplified side-view and pictorial illustrations of a transdermal delivery assembly, constructed and operative in accordance with another non-limiting embodiment of the present invention.
Figure 5B:
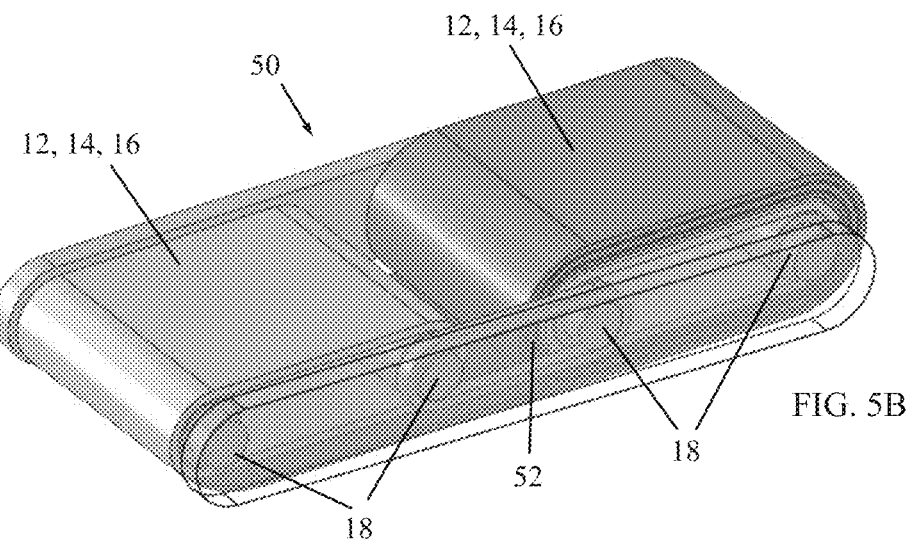

Reference is now made to FIGS. 5A and 5B, which illustrate a transdermal delivery assembly 50, constructed and operative in accordance with another non-limiting embodiment of the present invention. In this embodiment, two sets of patches 12 and non-patch zones 14 (e.g., stratum corneum resurfacing elements 14) are mounted on rollers 18. A driver 52 turns rollers 18 for driving patches 12 and stratum corneum resurfacing elements 14. One of the rollers may be the output shaft of driver 52 so that driver 52 directly drives the components. (As with all embodiments of the invention, the patch 12 may be used without non-patch zones 14.)

Figure 6A:
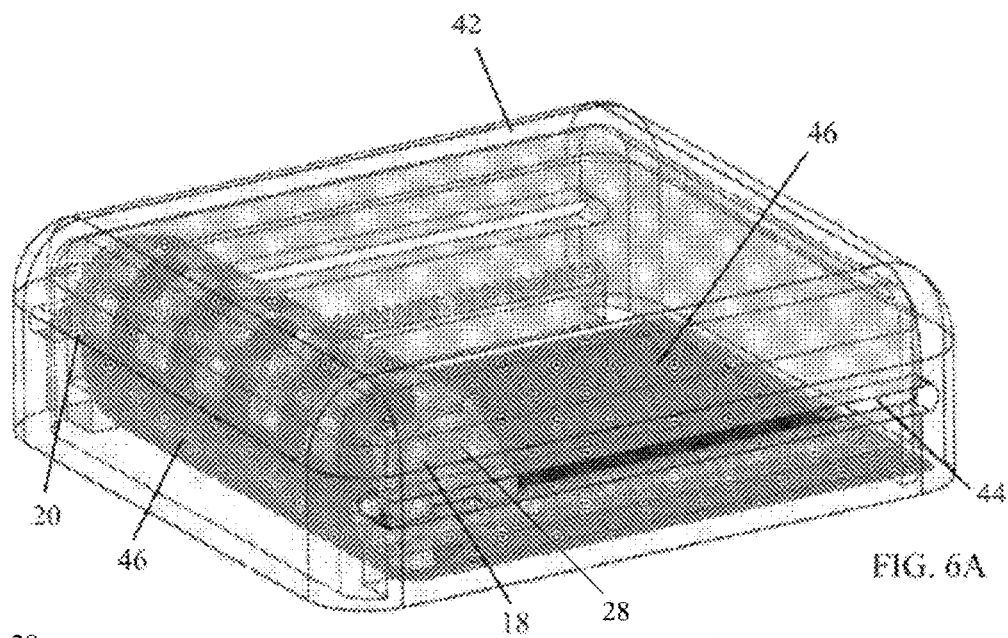
FIGS. 6A and 6B are simplified illustrations of placing the patch on the roller of the transdermal delivery assembly, and optionally removing a liner from the patch, in accordance with another non-limiting embodiment of the present invention.
Figure 6B:
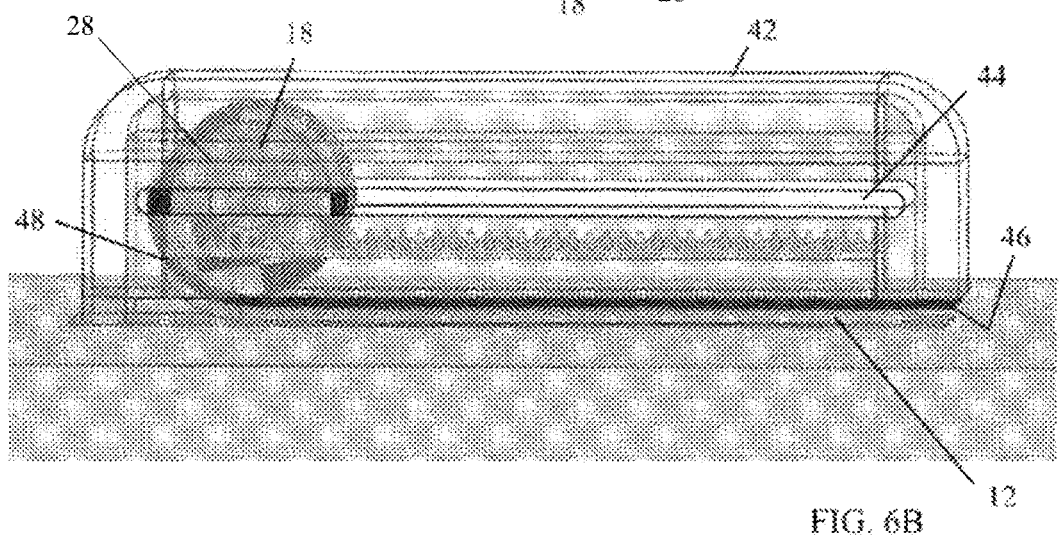

Reference is now made to FIGS. 6A-6B, which illustrate placing the patch 12 on the roller 18. Roller 18 may be disposed in a housing 42. Roller 18 may turn and move linearly in a track 44 (e.g., a toothed track) formed in housing 42. The driver 20 may turn roller 18 (driver 20 may be located inside the roller to save space). An adhesive foil 46 (without the substance on the patch) is connected to the roller 18 and extends out from the roller 18 over the bottom of housing 42. In order to connect the patch 12 to the roller, the housing 42 is placed on the patch 12, whereupon the patch 12 sticks to the adhesive foil 46. Then the driver 20 turns the roller 18 and causes the patch 12 to wrap and roll around the roller 18. The adhesive foil 46 then serves as a protective layer on the patch 12. Alternatively, instead of using driver 20, the housing 42 may be moved across a surface (e.g., assembly table) to cause roller 18 to turn and move in track 44. A thin tongue 48 may be provided near the roller 18 just before the patch 12 begins to wrap around the roller 12. The tongue 48 may catch and lift off any liner that was mounted on patch 12, so that patch 12 rolls up on roller 18 without the liner.

Figure 7A:
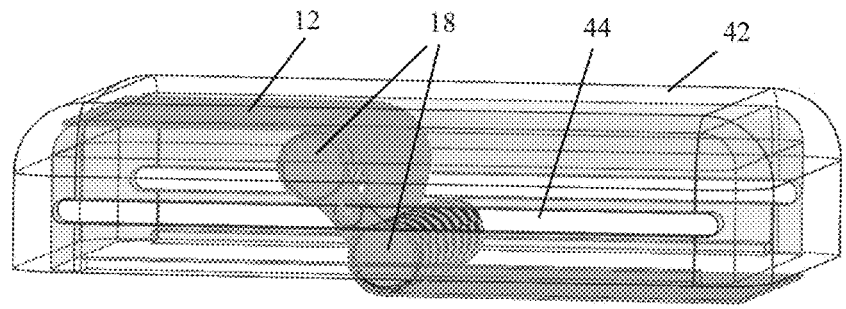
FIGS. 7A-7D are simplified illustrations of the patch on rollers of a transdermal delivery assembly, in accordance with another non-limiting embodiment of the present invention.
Figure 7B:
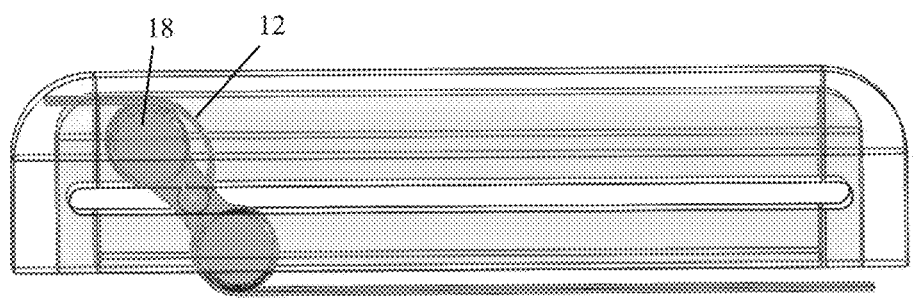
Figure 7C:
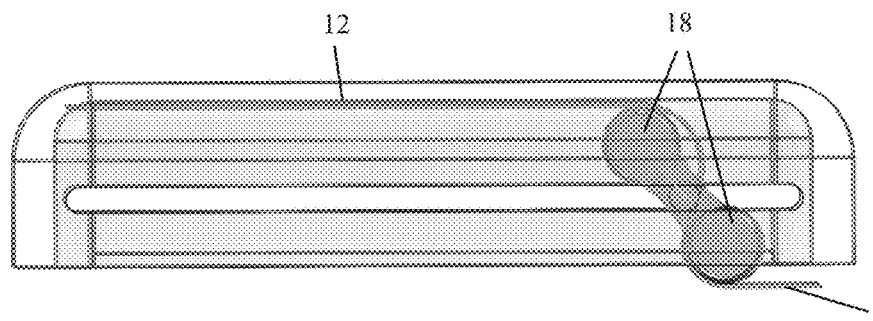
Figure 7D:
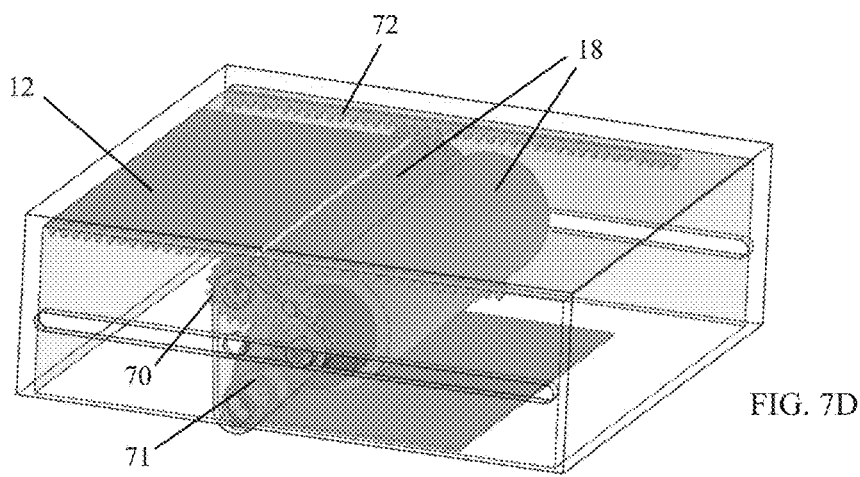

Reference is now made to FIGS. 7A-7B, which illustrate yet another embodiment of the patch 12 arranged on rollers 18. Here again, rollers 18 are disposed in housing 42 and turn and move linearly in track 44. In this embodiment, the patch 12 wraps around two sets of rollers 18 so that the patch 12 has an S-curve as it wraps around the rollers. This arrangement saves on space and maintains proper synchronization of the patch and roller motion, as well as of the housing motion (if desired). In FIG. 7D, the patch 12 wraps around more than two rollers 18, and one of the rollers is a gear 70, which is part of a gear train 71 that meshes with a gear rack 72. This arrangement provides precise control and synchronization of the patch and roller motion, as well as increasing torque and speed.

This embodiment with the two sets of rollers 18 rotated by the driver solves a potential problem. As the patch is laid out on the skin of the patient, the patch unrolls from the roller and sticks to the skin of the patient. As the patch is peeled off the skin, it starts to wrap around the roller. Depending on the diameter of the roller and adhesive properties of the patch (among other factors), if only one roller is used, as the patch wraps around the roller it can stick to itself, which makes it difficult if not impossible to re-deploy the patch, that is, unwrap the patch for subsequent placement on the skin. Large diameter rollers can solve this problem but have the disadvantage of increasing the size of the device. The embodiment with two sets of rollers 18 solves this problem by ensuring the patch does not stick to itself and does not significantly increase the size of the device. The additional roller or rollers cause the patch to travel a longer distance when getting peeled off and take the place of a single, large-diameter roller.

What is claimed is:

1. An assembly for controlling transdermal delivery of a drug to a skin of a patient comprising:
   a substrate including a patch; said patch impregnated with a substance adapted for transdermal delivery onto the surface of the skin;
   a driver operative to move said substrate to increase or decrease an area of contact between the substrate and the skin;
   a roller rotated by said driver; and
   a housing having a bottom surface configured for placement against the skin, wherein said substrate extends to said bottom surface of said housing and attaches to said bottom surface of said housing.

2. The assembly according to claim 1, further comprising an electronic controller that controls said driver, said controller operative to control for how long a portion of said patch is in contact with the skin.

3. The assembly according to claim 1, wherein said patch is mounted on said substrate, and said substrate is driven by said driver.

4. The assembly according to claim 3, wherein said substrate is mounted on one or more rollers.

5. The assembly according to claim 3, wherein said substrate further comprises a non-patch zone.

6. The assembly according to claim 1, wherein said driver is operatively linked to move said patch via a friction drive.

7. The assembly according to claim 1, wherein said driver is operatively linked to move said patch via a gear drive.

8. The assembly of claim 1, further comprising a repository for storing a portion of said patch while not in contact with said skin.

9. The assembly of claim 1, further comprising a roller, wherein a least a portion of said patch is wrapped around said roller.

10. The assembly of claim 9, further comprising a protective layer wrapped between layers of said patch wrapped on said roller.

11. The assembly of claim 9, wherein said driver rotates and moves said roller along said skin.

12. The assembly of claim 11, further comprising:
   a housing including a bottom surface configured for placement on said skin of said patient; and
   a track fixed to the housing; said track directed along said bottom surface and wherein said roller moves along said track while it rotates.

13. The assembly of claim 11, wherein said patch is wrapped around a roller in a wrapping direction and wherein said driver decreases said area of contact by rolling said roller in the wrapping direction to peel said patch off said skin and wrap said patch onto said roller.

14. The assembly of claim 11, wherein said patch is wrapped around said roller in a wrapping direction and wherein said driver increase said area of contact by rolling said roller in a direction opposite said wrapping direction to unwrap said patch from said roller.

15. The assembly of claim 1, wherein said patch includes a conventional transdermal drug patch configured for administering a drug according to a predetermined dosage schedule.

16. The assembly of claim 1, wherein said substrate includes patch and a non-patch zone and further comprising:
   a connector configured to attach to said non-patch zone of said substrate to said driver.

17. The assembly of claim 1, wherein said area of said patch in contact with said skin is detached from said substrate.

18. A controller for controlling transdermal drug administration to a skin of a subject comprising:
   a housing including a bottom surface configured for placement on said skin;
   a substrate including a patch; said patch impregnated with a substance adapted for transdermal delivery onto the surface of the skin; said substrate extending to said bottom surface of said housing and attached to said bottom surface of said housing, and
   a driver operative to move said patch to change an area of contact between the patch and the skin during the transdermal delivery.

19. The controller of claim 18, further comprising:
   an element movable with respect to said housing and coupled to said driver;
   a track directed along said bottom surface and wherein said element is coupled to the track such that when said driver moves said element to change said area of contact, said element moves along said track.

20. The controller according to claim 18, further comprising an electronic controller that controls said driver, said controller operative to control for how long a portion of said patch is in contact with the skin.

21. The controller according to claim 18, wherein said patch includes an adhesive for sticking said patch on the skin.

22. The controller according to claim 18, wherein said bottom surface includes an opening exposing said patch to said skin.

23. The assembly of claim 14, wherein said driver rotates said roller in a first direction and moves said roller along said skin to increase said area of contact with the skin and said driver rotates said roller in a second direction opposite said first direction and moves said roller along said skin to decrease said area of contact with the skin.

24. The assembly of claim 14, wherein said roller is configured to change said amount of contact by rotating to unwrap a first portion of said patch from the roller onto the skin while a second portion of said patch remains on the skin.

25. The assembly of claim 23, further comprising:
   a housing having a bottom surface configured for placement against the skin, and a track in said housing, said roller is coupled to the track to move along said track and across said bottom surface during said rotating.

26. The assembly of claim 25, wherein a coupling between said track and said roller is configured to synchronize moving along said track to said rotating such that said moving lays said patch onto the skin at a rate equal to the rate of unwrapping of the patch from the roller as a result of said rotating.

27. The assembly of claim 26, wherein a portion of said substrate extends from said roller to said bottom of said housing and is attached to said bottom surface of said housing.

28. The assembly of claim 1, wherein said driver is operative to control a dosing strength of the drug by moving the patch to change an amount of area of the patch touching the skin; said moving while at least a portion of said patch remains in contact with the skin.

29. The assembly of claim 28, further comprising an electronic controller controlling operation of said driver.

30. The assembly of claim 29, wherein said controller is preprogrammed to limit a dosage of said substance by removing said patch from the skin.

31. The assembly according to claim 1, wherein said patch includes an adhesive for sticking said patch on the skin.

32. The controller of claim 19, wherein said element includes a roller and wherein said driver is coupled to the roller for simultaneously rotating said roller in a first direction and translating said roller in along said bottom of the housing to peel said patch off said skin.

33. The controller of claim 32, wherein said substrate is attached to said roller and said driver is coupled to said roller for simultaneously rolling said roller in a second direction opposite said first direction and moving said roller across said bottom of the housing to place said patch onto the skin.

34. The controller of claim 32, wherein said patch is wrapped around said roller in a wrapping direction and wherein said driver increases said area of contact by rolling said roller in a direction opposite said wrapping direction to unwrap said patch from said roller.

* * * * *